United States Patent
Gulhar et al.

(10) Patent No.: US 10,065,315 B2
(45) Date of Patent: Sep. 4, 2018

(54) METHOD FOR OPERATING A ROBOTIC DEVICE AND ROBOTIC DEVICE

(71) Applicants: Abhinav Gulhar, Erlangen (DE); Philip Mewes, Nürnberg (DE); Sabine Thürauf, Forchheim (DE)

(72) Inventors: Abhinav Gulhar, Erlangen (DE); Philip Mewes, Nürnberg (DE); Sabine Thürauf, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/953,005

(22) Filed: Nov. 26, 2015

(65) Prior Publication Data

US 2016/0144510 A1 May 26, 2016

(30) Foreign Application Priority Data

Nov. 26, 2014 (DE) .................. 10 2014 224 122

(51) Int. Cl.
*A61B 17/00* (2006.01)
*B25J 9/16* (2006.01)
(Continued)

(52) U.S. Cl.
CPC .......... *B25J 9/1674* (2013.01); *A61B 8/4218* (2013.01); *A61B 34/30* (2016.02); *B25J 9/1633* (2013.01);
(Continued)

(58) Field of Classification Search
None
See application file for complete search history.

(56) References Cited

U.S. PATENT DOCUMENTS

| 4,967,126 | A | * | 10/1990 | Gretz | ...... B25J 9/1612 318/567 |
| 5,299,288 | A | * | 3/1994 | Glassman | ...... A61B 34/20 606/130 |

(Continued)

OTHER PUBLICATIONS

Bicchi Antonio et al.: "A Sensorized Minimally Invasive Surgery Tool for Detecting Tissutal Elastic Properties," in: Proceedings of the 1996 IEEE International Conference on Robotics and Automation Minneapolis, Minnesota—Apr. 1996, pp. 884-888.

(Continued)

*Primary Examiner* — Ryan Rink
(74) *Attorney, Agent, or Firm* — Lempia Summerfield Katz LLC (57) ABSTRACT

A method for operating a robotic device with a kinematic chain of mobile components is provided. The kinematic chain includes a function-specific end-effector at one end. Sensor values are acquired by sensors of the robotic device arranged on the kinematic chain or in the environment of the kinematic chain. A force acting on the end-effector or another component of the kinematic chain, or a variable dependent thereupon, is determined in a prespecified manner based on the acquired sensor values. The force or variable determined is compared with a prespecified first safety limit value by a control mechanism of the robotic device. A characteristic of the kinematic chain or the function-specific end-effector is adapted if the force or variable determined is in a prespecified relationship to the first safety limit value in order to increase the operational safety of a robotic device and of people in the environment of the robotic device.

23 Claims, 2 Drawing Sheets

(51) Int. Cl.
*A61B 8/00* (2006.01)
*A61B 34/30* (2016.01)
*A61B 1/00* (2006.01)
*A61B 10/04* (2006.01)
*A61B 17/70* (2006.01)
*A61B 90/00* (2016.01)

(52) U.S. Cl.
CPC ........... *B25J 9/1653* (2013.01); *B25J 9/1694* (2013.01); *A61B 1/00149* (2013.01); *A61B 8/429* (2013.01); *A61B 17/7082* (2013.01); *A61B 17/7089* (2013.01); *A61B 2010/045* (2013.01); *A61B 2090/064* (2016.02); *G05B 2219/39305* (2013.01); *G05B 2219/40201* (2013.01); *G05B 2219/45117* (2013.01); *Y10S 901/04* (2013.01); *Y10S 901/09* (2013.01)

(56) References Cited

U.S. PATENT DOCUMENTS

| | | | | |
|---|---|---|---|---|
| 5,343,385 | A * | 8/1994 | Joskowicz | B25J 9/1664 700/255 |
| 9,456,800 | B2 * | 10/2016 | Anthony | A61B 8/4209 |
| 9,592,608 | B1 * | 3/2017 | Bingham | B25J 9/1674 |
| 2004/0174130 | A1 * | 9/2004 | Inoue | B23Q 17/09 318/569 |
| 2005/0200324 | A1 * | 9/2005 | Guthart | A61B 34/20 318/568.11 |
| 2007/0162164 | A1 * | 7/2007 | Dariush | B25J 9/1602 700/61 |
| 2009/0062813 | A1 | 3/2009 | Prisco et al. | |
| 2009/0099692 | A1 * | 4/2009 | Prisco | A61B 19/22 700/254 |
| 2010/0049352 | A1 * | 2/2010 | Kohlmaier | B25J 9/1633 700/103 |
| 2010/0137918 | A1 * | 6/2010 | Wilcox | A61B 17/7037 606/301 |
| 2010/0228264 | A1 * | 9/2010 | Robinson | A61B 18/1206 606/130 |
| 2010/0280663 | A1 * | 11/2010 | Abdallah | H01R 13/17 700/264 |
| 2011/0125138 | A1 * | 5/2011 | Malinouskas | A61B 17/068 606/1 |
| 2011/0130876 | A1 * | 6/2011 | Gao | B25J 9/1633 700/258 |
| 2011/0309782 | A1 * | 12/2011 | Bonin | H02P 21/50 318/611 |
| 2012/0059378 | A1 * | 3/2012 | Farrell | A61B 17/1626 606/80 |
| 2013/0012930 | A1 * | 1/2013 | Ruiz Morales | B25J 13/085 606/1 |
| 2013/0073084 | A1 * | 3/2013 | Ooga | B25J 9/1633 700/254 |
| 2013/0110130 | A1 * | 5/2013 | Manzo | A61B 1/00149 606/130 |
| 2013/0150860 | A1 * | 6/2013 | Sidebotham | A61B 17/1666 606/81 |
| 2013/0226197 | A1 * | 8/2013 | Diolaiti | G05B 19/19 606/130 |
| 2013/0231678 | A1 * | 9/2013 | Wenderow | A61B 19/2203 606/130 |
| 2013/0231681 | A1 * | 9/2013 | Robinson | A61B 18/1206 606/130 |
| 2013/0236050 | A1 * | 9/2013 | Choi | G06K 9/00201 382/103 |
| 2014/0171778 | A1 * | 6/2014 | Tsusaka | A61B 5/6843 600/407 |
| 2014/0236222 | A1 * | 8/2014 | Tegels | A61B 17/0057 606/213 |
| 2014/0379126 | A1 * | 12/2014 | Ueberle | B25J 9/1674 700/245 |
| 2015/0038980 | A1 * | 2/2015 | Merscher | A61B 19/2203 606/130 |
| 2016/0374768 | A1 * | 12/2016 | Griffiths | B25J 9/1633 606/130 |
| 2017/0128082 | A1 * | 5/2017 | Philipp | A61B 17/1622 |

OTHER PUBLICATIONS

Wagner, Christopher R. et al.: "The Role of Force Feedback in Surgery: Analysis of Blunt Dissection," in: Presented at the Tenth Symposium on Haptic Interfaces for Virtual Environment and Teleoperator Systems, Mar. 24-25, 2002, Orlando.

* cited by examiner

FIG 3

METHOD FOR OPERATING A ROBOTIC DEVICE AND ROBOTIC DEVICE

CROSS-REFERENCE TO RELATED APPLICATIONS

The present patent document claims the benefit of DE 102014224122.7, filed on Nov. 26, 2014, which is hereby incorporated by reference in its entirety.

TECHNICAL FIELD

The present embodiments relate to a method for operating a robotic device with a kinematic chain of mobile components including a function-specific end-effector at one end of the kinematic chain. The present embodiments further relate to a robotic device including a kinematic chain of mobile components.

BACKGROUND

Strict requirements are placed on modern robotic devices. For example, strict requirements apply to medical-robotic devices (e.g., when the medical-robotic devices assist or carry out minimally-invasive interventions). The use of robotic devices in minimally-invasive interventions has numerous advantages. However, if the characteristics of the robotic device are not set to the optimum degree (e.g., if the force exerted by the robotic device is too high), fatal consequences may ensue. In other fields of robotics, it is also important to perform a pre-specified procedure in a changing environment with a high degree of precision and flexibility without incurring unwanted damage.

SUMMARY AND DESCRIPTION

The present embodiments may obviate one or more of the drawbacks or limitations in the related art. For example, one or more of the present embodiments may increase the operational safety of a robotic device (e.g., the safety of people in the environment of the robotic device).

According to the present embodiments, a method is provided for operating a robotic device with a kinematic chain of mobile components, where the kinematic chain includes a function-specific end-effector or a function-specific terminal element at one end of the kinematic chain. The method includes the acquisition of respective sensor values by sensors arranged on the kinematic chain or in the environment of the kinematic chain. The sensors may, for example, take the form of torque sensors and/or force sensors. A force applied to the end-effector or another component of the kinematic chain or a variable dependent upon the applied force is determined in a prespecified manner based on the acquired sensor values. The dependent variable may be torque. The force or variable determined is compared with a prespecified first safety limit value by a control mechanism of the robotic device. A characteristic of the kinematic chain or of the function-specific end-effector is adapted if the determined force or variable is in a prespecified relationship to the first safety limit value.

A precise and flexible setting of the respective acting force or the variable dependent upon the force dependent may be provided. A situation-dependent optimum characteristic of the robotic device may be set. This enables damage or, in the case of a medical-robotic device, injuries to be avoided because mechanical energy introduced by the robotic device into a workpiece or a patient may be set precisely. Precisely with a medical-robotic device, this enables the avoidance of damage to healthy anatomical structures, such as, for example, organs or bones. Because the adaptation of the situation-dependent optimum characteristic provides an automatic, flexible safety margin, the operational safety of the robotic device is increased, and the risk of injuries to people in the environment of the robotic device is reduced. The user friendliness may also be improved by the adaptation of the situation-dependent optimum characteristic.

In an embodiment, the situation-dependent optimum characteristic includes a parameter of the kinematic chain as a spring-damper system. For example, the parameter may be a rigidity and/or a damping of the kinematic chain, a torque acting on the end-effector, a force acting on the end-effector, a speed of the end-effector, an acceleration of the end-effector, or any combination thereof. The situation-dependent optimum characteristic may also include a position and/or orientation of the end-effector. The acting torque and/or the acting force may be a torque exerted by the end-effector and/or a force exerted by the end-effector. Different models may be used for the description of the kinematic chain as a spring-damper system. Because the aforementioned characteristics may result in damage or injuries in the event of a faulty setting, it is advantageous to adapt precisely these situation-dependent optimum characteristics. It has been found that it is difficult for an operator to estimate a rigidity of the kinematic chain and a torque acting on the end-effector or a force acting on the end-effector. Therefore, the adaptation of precisely these situation-dependent optimum characteristics is particularly advantageous.

In another embodiment, the situation-dependent optimum characteristic includes a temporal change in the rigidity, the torque, the force, the speed, the acceleration, or any combination thereof. A more precise acquisition of an actual movement of the robotic device is possible via the situation-dependent optimum characteristics. Hence, the situation-dependent optimum characteristic may also be adapted more precisely, or the safety limit value may be better adapted to the actual circumstances.

A geometry of the mobile components and/or of the end-effector is taken into account during the determination of the force or variable. Thus, the force or variable may be determined precisely so that precise adjustment of the first safety limit value is possible.

In an embodiment, the adaptation is performed if the determined force or variable is greater than the first safety limit value. The function "greater than" then corresponds to the prespecified relationship to the first safety limit value. The comparison may be performed with reference to absolute values (e.g., that disregard a direction that may be expressed in a preceding sign of a variable). This is advantageous if the situation-dependent optimum characteristic includes the torque, the force, the speed, the acceleration, or any combination thereof because high values for these characteristics generally represent a high risk. The adaptation of the characteristic may include a reduction of the characteristic (e.g., the speed and/or the acceleration). A first safety limit value may be used to prespecify the permitted maximum values for the determined force or variable to limit risk or damage and to increase the safety of the robotic device.

In an embodiment, prespecification of the first safety limit value is provided depending on a property and/or a suitability of the function-specific end-effector of the kinematic chain. A plurality of interchangeable end effectors with different functional specifications, and hence fields of application, for which the safety limit value may be adapted, may be provided. The plurality of interchangeable end effectors increases the flexibility of the robotic device. The respective first safety limit value for the respective end-effector may also be prespecified individually so that precise adaptation of the characteristic to a respective procedure to be performed (e.g., automatically) is possible. Corresponding safety margins are automatically adapted to the respective end-effector used, reducing the respective risk or damage potential.

In an embodiment, the prespecification of the first safety limit value is performed in dependence on a prespecified force and/or torque application on the function-specific end-effector, and/or is performed in dependence on an effect of a prespecified force and/or torque by the function-specific end-effector. The first safety limit value may be prespecified for a procedure in which prespecified force and/or torque applications, and/or force and/or torque effects in combination with force and/or torque actions, are to be expected. The force and/or torque effect by the function-specific end-effector may provide a force and/or torque effect by a tool attached to the function-specific end-effector. The prespecified force and/or torque effect by the function-specific end-effector may take place on another device or on a person (e.g., a patient or a part of a patient). The force and/or torque application may be effected by a person (e.g., a patient or a part of a patient or an operator or another device). For example, in a specific operational phase during operation, the prespecified force and/or torque application, and/or the prespecified force and/or torque effect may be a desired or expected force and/or torque action.

The first safety limit value enables the safety margins to be adapted to different operational phases of the robotic device. This can also exclude the possibility of impairment of the operation due to unsuitable safety margins (e.g., if in one operational phase, the occurrence of particularly high forces, speeds or torques is deliberately intended). Additionally, the force and/or torque effect intended in an operational phase of the robotic device may be precisely controlled and set since the adaptation of the characteristic does not interfere with the force and/or torque effect exerted by the device, and the intended force and/or torque effect is not falsified.

The respective force and/or torque action may be provided (e.g., the respective application or effect is based on a prespecified change to a force and/or torque). The change to a force and/or torque may be standardized to a prespecified amount for a distance covered by a function-specific terminal element of the kinematic chain. Therefore, the prespecified force and/or torque action may be defined via a change to a force and/or torque for each distance. The respective force and/or torque action and corresponding actions of the robotic device may be set precisely.

The prespecified force and/or torque application is effected by an operational action on the robotic device (e.g., a guidance of the kinematic chain by an operator's hand), and/or the prespecified force and/or torque effect by the device includes a sequence of an operational action. The operational action may be an operational action in a gravitation-compensation mode of the robotic device. In a gravitation-compensation mode, in dependence on an acquired force and/or on an acquired torque, a movement of the robotic device (e.g., the end-effector) is effected in the direction of the force exerted. The influence of the gravitation force is automatically compensated. The robotic device may be guided by an operator in that the operator uses a hand to exert a force on the end-effector or another mobile component of the kinematic chain in a desired direction of movement.

A precise prespecification of a force and/or torque application and a force and/or torque effect is possible so that the prespecification of the first safety limit value enables precise setting of a suitable safety margin. It is also possible, for example, to compensate counter movements of external origin (e.g., a patient's reflexes) on a prespecified force and/or torque effect by the robotic device. Compensation reduces or excludes the falsification of a target force and/or torque effect and increases the safety of the robotic device.

A position of a structure assigned to the prespecified force and/or torque application (e.g., an anatomical structure) may be determined by a position and/or orientation of the function-specific end-effector at the time of the prespecified force and/or torque application, or at the time of the adaptation. The anatomical structure may, for example, be an organ, a tumor, a bone, or any combination thereof. In this way, a structure may be assigned to a prespecified force and/or torque application via a known mechanical property of the structure. For example, it may be known that a tumor is more solid than an organ surrounding the tumor. Therefore, force and/or torque application on the end-effector will be lower on the penetration of the surrounding organ than the force and/or torque application is on the penetration of the tumor. Therefore, if the determined force or variable applied to the end-effector force corresponds at a particular time to a force and/or torque application for the prespecified tumor, then the position of the end effector corresponds to a position of the tumor. The first safety limit value may be selected such that the characteristic is adapted at the time of the occurrence of the prespecified force and/or torque application, enabling the prevention of a force on the tumor, or more generally on the structure assigned to the force and/or torque. This enables a further, possibly dangerous, penetration of the end-effector or of a tool of the end-effector into the anatomical structure, or the deformation may be prevented. Sampling and identification of structures is enabled in that a series of position and/or orientation determinations is used to identify a series of positions and/or orientations from which a surface of the structure may be determined. From the determined surface, it is possible to determine a force and/or a size of the structure and identify the structure. For example, the size of a tumor may be determined. For example, this knowledge may be used for diagnostic purposes or to define a spatial region in which a prespecified safety limit value applies.

The end-effector may be placed on a surface of structure without this structure being damaged, deformed or displaced. This also enables the position of the structure to be determined without further measures being necessary. For example, in a medical procedure, further acts such as, for example, an imaging method entailing radiation exposure or use of other devices (e.g., used for the acquisition of a position of an anatomical structure) may be avoided. As a result, the end-effector may be positioned with greater precision. Moreover, a greater degree of comfort may be provided using fewer devices and without additional method acts.

In an embodiment of the method, it is provided that a second (e.g., higher) safety limit value is prespecified, and the force or variable determined is also compared with the second safety limit value. A warning signal is also output to an operator when the determined force or variable is in a prespecified relationship to the second safety value (e.g., when the determined force or variable is greater than the second safety limit value). The warning signal may be a visible and/or audible warning signal. The warning signal enables warnings to be given of particularly dangerous situations. If the second safety limit value is higher than the first safety limit value, an operator may be notified of a dangerous exceeding of the first safety limit value. This even occurs if, for example, due to mass inertia of the robotic system, adaptation has not yet taken place or has not taken place at the speed required. If the second safety limit value is below the first safety limit value, the operator is made aware of the imminence of a critical situation, such as is represented by the first safety limit value.

Adaptation of the characteristic takes place in a plurality of acts, and at the same time, a warning is output in each case to the operator in one or more of the acts, avoiding an adaptation that surprises the operator. Further, no ill-considered reflexes on the part of the operator (e.g., that possibly present a danger) are to be expected.

An embodiment of the method provides the prespecification of a first and second value for the first safety limit value and the selection of the first or second value as the first safety limit value for the comparison with the force or variable. For example, two different operating modes may be set for the robotic device, between which it is possible to switch to and fro by the selection of the first or second value for the first safety limit value. For example, it is possible for a "locked mode" to be implemented in that, for example, the first value is negative, so that the safety limit value is already exceeded by a stationary end-effector with no force applied apart from gravitational force. For example, the rigidity may thus be adapted to a prespecified high value so that the end-effector is in effect blocked in the resting position and/or resting orientation. Alternatively, in a "locked mode," no movement of the robotic device is possible. The "locked mode" may be activated directly. Flexibility of the robotic device is increased. Switching between modes or switching modes on and off may achieve a rapid adaptation of the robotic device to a changed situation resulting in increased safety.

In an embodiment, the first safety limit value is prespecified depending on the acquired sensor values. Prespecification may be performed depending on sensor values acquired over a prespecified period of time. A breakaway torque may be achieved. A breakaway torque causes a resting end-effector to require a force or variable exceeding a minimum value (e.g., 3 Newton (N)) as an operational action in order to be put into movement. As soon as the minimum force is applied, the end-effector is free moving. If the force of the operational action falls below a further limit amount (e.g., 1 Newton) the end-effector may be blocked against movement.

Behavior of this kind, may, for example, be achieved in that the first safety limit value that is first set to zero or a negative amount so that the first safety limit is exceeded by the force or variable determined in a resting position and/or resting orientation of the end-effector. An operational action with a force (e.g., 2 Newton) does not result in any movement of the end-effector. If the force or variable determined takes on a value above the minimum value (e.g., more than 3 Newton), the first safety limit value is raised to an elevated value (e.g., 10 Newton), and the end-effector is freely movable. If the force or variable determined falls below a further prespecified value (e.g., to less than 1 Newton), the safety limit value is reduced to the previous (e.g., negative) value. Correspondingly, the characteristic is adapted to the fact that the safety limit value has been exceeded, resulting in the resting or blocking of the end-effector.

Sudden, unexpected changes in the sensor values may result in an adaptation of a characteristic independently of prefixed limit values. For example, in dependence on operational phases, in which specific values are usual for specific characteristics, different safety buffers may be implemented. The flexibility of the robotic device is maximized, and safety is improved.

In an embodiment, the prespecification of the first safety limit value is performed depending on a position and/or orientation of the function-specific end-effector of the kinematic chain and/or of a joint angle between two mobile components of the kinematic chain. The position and/or orientation may, for example, be determined relative to a further predetermined position and/or orientation. For example, the further prespecified position and/or orientation may include an anatomical structure (e.g., an organ and/or a tumor). The first safety limit value may be prespecified depending on a distance of the end-effector from the further predetermined position. On approaching a specific position and/or orientation, the characteristic may be adapted via the prespecification of the first safety limit value depending on the position and/or orientation and hence, for example, on the distance. The safety limit value and the safety margins may be adapted flexibly to a situation. Thus, a high degree of safety of the robotic device is combined with ease of handling. The handling may be adapted to individual conditions of a spatial type.

It is possible to check within which of a plurality of predetermined spatial regions the position of the function-specific end-effector is located and to take account of a result of the check during the prespecification of the first safety limit value depending on the position, the orientation, the joint angle, or any combination thereof. The predetermined spatial regions may be spatial regions in the interior of a patient that may be adopted by respective anatomical structures (e.g., bones and/or organs). The spatial regions may also be respective regions surrounding anatomical structures in the interior of a patient. The check may be restricted to a check as to whether the position of the end-effector is within a predetermined spatial region.

For example, corresponding spatial regions and the prespecification of a respective valid first safety limit value may support the avoidance of an anatomical structure of a patient (e.g., a sensitive organ or a bone) by the function-specific end-effector or by a tool attached to the end-effector. An unintentional introduction of the end-effector into a spatial region is prevented. In this way, the safety of the robotic device is increased overall.

In an embodiment, the first safety limit value (S) is prespecified depending on a joint-angle value of a joint and/or a combination of joint-angle values of several joints between mobile components of the kinematic chain. It is possible to check whether the joint-angle value or values are within one or more prespecified region or regions. Movement of the robotic device or of the kinematic chain into angular regions, in which the movement possibilities of the robotic device, and hence, for example, evasion possibilities are reduced, may be avoided. For example, movement of a joint into an associated border zone in which a specific movement of the joint is no longer possible and, for example, compensated by a combination of movements of other joints (e.g., to achieve an equivalent movement of the robotic device) may be prevented.

The characteristic may be adapted when the force or variable is below the first safety limit value if the acquired sensor values adopt predetermined values for a prespecified time interval. For example, an adaptation is performed when the acquired values for a prespecified time interval represent the resting of the end-effector. In the case of non-operation for a prespecified time interval, there may be an adaptation of the characteristic in the form of a blockage of movements of the end-effector. In a resting phase of the robotic device in which the robotic device does not receive any operational action, unnoticed slight movements of the robotic device (e.g., drifting) are prevented.

In an embodiment, the adaptation includes the restriction of a movement of the function-specific end-effector and/or a mobile component by at least one joint or a combined movement around a plurality of joints of the kinematic chain (e.g., by the reduction of the movement of the function-specific end-effector by a degree of freedom). The degree of freedom may be a rotary and/or translatory degree of freedom in a Cartesian reference system, restricting the movement or movements of a joint or a combination of joints. Due to the restriction of the movement, a human operator is able to predict the behavior of the end-effector, reducing the risk of injuries, falls, and increasing safety. Particularly dangerous movements for a patient may be excluded, or specific spatial regions may be blocked for the end-effector. Precisely restricting a movement by a combination of joints enables flexible restriction of the behavior of the robotic device. It is also possible to flexibly restrict a first joint by restricting one or more joints such that the robotic device may be operated while retaining the restriction in an optimum parameter range for the robotic device.

In an embodiment of the method, the robotic device is a medical-robotic device (e.g., a medical-surgical device) that may be used in a medical-surgical and/or medical-diagnostic procedure. The robotic device may be a holding device for a biopsy needle or for a pedicle screw, or for an endoscope or an ultrasound device. A precisely controllable force may be exerted on the patient or an anatomical structure of the patient, avoiding damage outside a prespecified region to be operated on. In a holding device, damage to an anatomical structure surrounding the region to be operated on may be prevented because a force guided by the holding device is transmitted in a targeted manner. In a diagnostic device, such as, for example, an ultrasound device, very precise positioning may be enabled.

The prespecified force and/or torque application on the medical-robotic device is achieved by a movement of a partial region of the patient. A prespecified anatomical structure of the patient and/or the prespecified force and/or torque effect is achieved by the medical-robotic device on a partial region of the patient (e.g., on a prespecified anatomical structure of the patient). It is possible to set a prespecified force between the anatomical structure and the robotic device such that the robotic device is automatically held in a prespecified position and/or orientation relative to an anatomical structure, even if the anatomical structure is moving. Movements by the patient or partial regions of the patient (e.g., caused by beating of the heart, respiration, movement or by reflexes) are automatically compensated. In this way, damage to a region of the patient adjacent to the end-effector from a movement of this kind is prevented.

The present embodiments also include a robotic device with a kinematic chain of mobile components including a function-specific end-effector at one end of the kinematic chain and a plurality of sensors arranged on the kinematic chain and configured to acquire respective sensor values. The robotic device may also include a plurality of kinematic chains. The robotic device is an automated (e.g., partially or fully automated) robotic device. A tool attached to the function-specific end-effector may be considered to be part of the end-effector and thus part of the kinematic chain. The robotic device also includes a control mechanism configured, based on the acquired sensor values, to determine a force applied to the end-effector or a variable dependent on this force in a prespecified manner, to compare the force or variable determined with a prespecified first safety limit value, and to adapt a characteristic of the kinematic chain or of the function-specific end-effector if the force or variable acquired is in a prespecified relationship to the first safety limit value. The control mechanism is configured to adapt the characteristic if the force or variable acquired is greater than the first safety limit value. Advantages and advantageous embodiments correspond to the advantages and advantageous embodiments of the method.

In an embodiment, the robotic device includes a device (e.g., cameras and/or pressure sensors on an external surface of the robotic device) to prevent an unwanted movement of the mobile components (e.g., mobile components that are different from the end-effector) in a spatial region occupied by a person and/or to avoid or give way to a person who enters a spatial region occupied by the robot so that the robotic device is suitable for man-robot cooperation. The robotic device or mobile component of the robotic device may be guided and controlled safely by an operator. The robotic device may be flexibly adapted to the changing requirements of man-robot cooperation and easily used in different scenarios. Precisely during usage in different scenarios such as are to be expected with a medical-robotic device, an automatically adjusting or an easily adaptable safety margin, such as that offered by one or more of the present embodiments, is advantageous.

DETAILED DESCRIPTION

Figure 1:
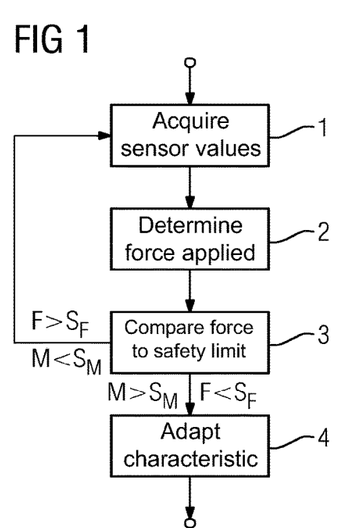
FIG. 1 depicts a schematic of a flow diagram of a first exemplary embodiment of a method for operating a robotic device.

FIG. 1 is a schematic depiction of a flow diagram of a first embodiment of a method for operating a robotic device. The method includes four successive acts that may be repeated. Thus, the method is performed quasi-continuously. In the present example, the robotic device is a medical-robotic device with a kinematic chain of mobile components. The kinematic chain includes a function-specific end-effector (e.g., a drill) at an end.

Acquisition 1 of respective sensor values by sensors arranged on the kinematic chain is performed. In the example depicted, the sensors are provided as torque sensors on joints of the kinematic chain. Determination 2 of a force F applied to the end-effector (e.g. a drill) based on the acquired sensor values is performed. For example, if the end-effector is operating (e.g., drilling a bone), the determined force F will be applied to the end-effector parallel to a drilling axis.

Comparison 3 of the force F determined with a prespecified first safety limit value $S_F$ is performed. Therefore a force F exerted parallel to the drilling axis on the drill end-effector is compared with a prespecified first safety limit value $S_F$. If the drill is still inside the bone, the drill is opposed by a significant resistance such that the force F determined exceeds the first safety limit value $S_F$. Correspondingly, acquisition 1 of respective sensor values is continued, and no adaptation 4 to a characteristic is performed.

If the drill drills through the bone, the resistance reduces abruptly in the direction of the drilling axis, and the force F determined on the end-effector in the direction of the drilling axis will fall below the prespecified first safety limit value $S_F$. Correspondingly, adaptation 4 of a characteristic of the kinematic chain or function-specific end-effector is performed. This takes place such that the speed of the end-effector in the direction of the drilling axis is set to zero so that the end-effector does not drill into healthy tissue surrounding the bone.

Alternatively or additionally, the determination 2 may also relate to a torque M applied to the end-effector (e.g., the drill) as a variable dependent on a force. In this example, during the comparison 3, the torque M is compared with a prespecified first safety limit value $S_M$ matched to expected values of the torque M. For example, a uniform torque M may be expected during a correctly performed drilling procedure. Therefore, the comparison 3 provides a torque M below the prespecified first safety limit value $S_M$. Correspondingly, no adaptation 4 is performed, and the drilling procedure and the acquisition 1 of the corresponding sensor values are continued.

For example, if the drill becomes skewed in the bone (e.g., due to a movement of the patient), the torque M will rise abruptly. Correspondingly, the comparison 3 reveals that the torque M exceeds the first prespecified first safety limit value $S_M$. Adaptation 4 of a characteristic of the function-specific end-effector is performed, reducing the torque M to zero (e.g., the drilling procedure is stopped). Damage to the bone is avoided, and the precision of the drill hole is retained to the greatest degree possible.

Figure 2:
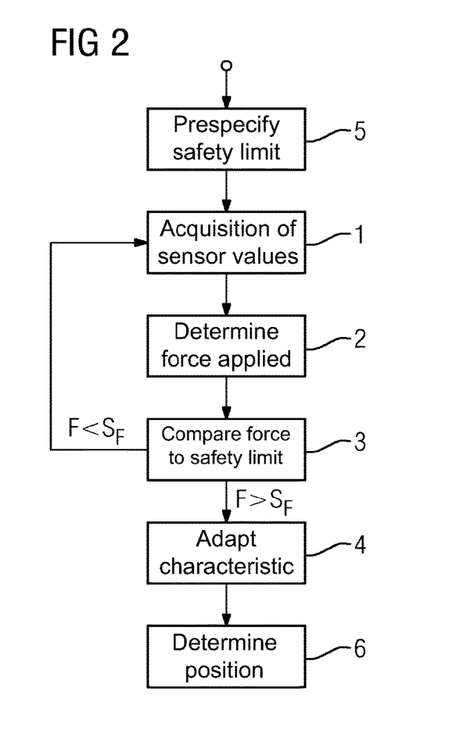
FIG. 2 depicts a schematic of a flow diagram of a second exemplary embodiment of a method for operating a robotic device.

FIG. 2 is a schematic depiction of a flow diagram of a second exemplary embodiment of a method for operating a robotic device. In the present example, the function-specific end-effector of the kinematic chain of the robotic device is embodied as a needle. For example, the needle is introduced along an axis into a patient in order to localize a tumor and/or to take a sample from the tumor.

In the present example, the tumor is known to have a solidity greater than a solidity of the tissue surrounding the tissue, or the tumor has a solidity in a known range. Thus, the arrival of the needle at the tumor effects a prespecified force application on the function-specific end-effector (e.g., the force application at the tumor differs from the force application on the penetration of the tissue surrounding the tumor).

Correspondingly, prespecification 5 of the first safety limit value $S_F$ depends on the prespecified force applied on the function-specific end-effector, which is expected when the needle arrives at the tumor. While the end-effector is moved (e.g., when the needle is introduced into the patient), continuous acquisition 1 of the respective sensor values by the sensors arranged on the kinematic chain is performed.

Determination 2 of the force F applied to the end-effector based on the sensor values is performed. A comparison 3 of the force F determined with the prespecified first safety limit value $S_F$ is performed by a control mechanism of the robotic device. In this example, further movement of the end-effector only takes place if the determined force F does not exceed the first safety limit value $S_F$. Correspondingly, the needle is introduced further into the patient as long as the needle has not reached the tumor.

If the needle reaches the tumor, the mechanical resistance on the needle increases, and the determined force F exceeds the first safety limit value $S_F$. Correspondingly, adaptation 4 of a characteristic of the function-specific end-effector is performed (e.g., setting the speed of the end-effector in the direction of the needle axis to zero). Determination 6 of a position of the function-specific end-effector is performed. The position of the tumor may be determined from the position of the function-specific end-effector. Localization of tumors and other anatomical structures (e.g., organs) may be enabled. Adaptation 4 of the characteristic (e.g., a speed of the end-effector or a force F acting on the end-effector) enables deformation or injury to the localized organ or the localized anatomical structure to be avoided.

Figure 3:
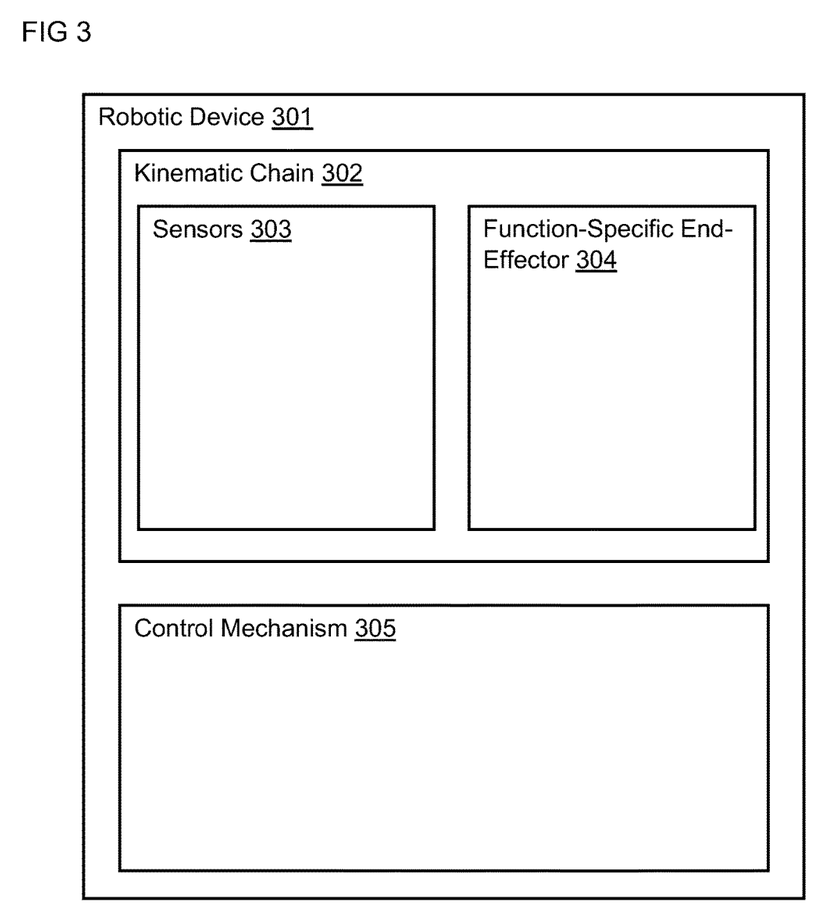
FIG. 3 depicts a schematic view of a block diagram of an exemplary embodiment of a robotic device.

FIG. 3 is a schematic depiction of a robotic device 301 with a kinematic chain 302 of mobile components including a function-specific end-effector 303 at one end of the kinematic chain and a plurality of sensors 304 arranged on the kinematic chain 302. The robotic device 301 also includes a control mechanism 305. The control mechanism 305 may be configured to cause the robotic device 301 to perform the methods discussed above.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a robotic device with a kinematic chain of mobile components, wherein the kinematic chain comprises a function-specific end-effector at one end, the method comprising:
   acquiring respective sensor values using sensors of the robotic device arranged on the kinematic chain or in an environment of the kinematic chain;
   determining a force applied to the function-specific end-effector or another component of the kinematic chain, or a variable dependent on the force, in a prespecified manner based on the acquired sensor values;
   prespecifying, automatically based on a medical-surgical or medical-diagnostic procedure, a first safety limit value based on a suitability of the function-specific end-effector of the kinematic chain for the procedure;
   comparing the force or the variable with the prespecified first safety limit value by a control mechanism of the robotic device; and
   adapting a characteristic of the kinematic chain or a characteristic of the function-specific end-effector when the force or the variable is in a prespecified relationship to the first safety limit value.

2. The method of claim 1, wherein the characteristic includes a parameter of the kinematic chain represented as a spring-damper system, wherein the parameter comprises one or more of: rigidity, damping of the kinematic chain, torque acting on the function-specific end-effector, a force acting on the function-specific end-effector, speed of the function-specific end-effector, and acceleration of the function-specific end-effector.

3. The method of claim 1, wherein the adapting is performed when the force or the variable is greater than the first safety limit value.

4. The method of claim 1, wherein the prespecifying of the first safety limit value is based on a property of the function-specific end-effector of the kinematic chain and the suitability of the function-specific end-effector of the kinematic chain for the procedure.

5. The method of claim 1, wherein the prespecifying of the first safety limit value is based on:
application of a prespecified force, a prespecified torque, or the prespecified force and the prespecified torque on the function-specific end-effector,
application of the prespecified force, the prespecified torque, or the prespecified force and the prespecified torque by the function-specific end-effector, or
application of the prespecified force, the prespecified torque, and the prespecified force and the prespecified torque on the function-specific end-effector and by the function-specific end-effector.

6. The method of claim 5, wherein the prespecified force application, the prespecified torque application, or the prespecified force application and the prespecified torque application is based on a prespecified change to a force, a torque, or the force and the torque,
wherein the prespecified force application, the prespecified torque application, or the prespecified force application and the prespecified torque application is standardized to a prespecified value for a distance covered during the procedure by the function-specific end-effector, a mobile component of the kinematic chain, or the function-specific end-effector and the mobile component of the kinematic chain.

7. The method of claim 5, wherein the prespecified force application, the prespecified torque application, or the prespecified force application and the prespecified torque application is effected by an operational action or a sequence of operational actions on the robotic device.

8. The method of claim 7, wherein the operational action on the robotic device comprises guidance of the kinematic chain by a hand of an operator.

9. The method of claim 5, further comprising:
determining a position of a structure assigned to the prespecified force application, the prespecified torque application, or the prespecified force application and the prespecified torque application, wherein the determining of the position comprises determining a position, an orientation, or the position and the orientation of the function-specific end-effector at a time of the prespecified force application, the prespecified torque application, or the prespecified force application and the prespecified torque application or at a time of the adaptation.

10. The method of claim 1, further comprising:
prespecifying a second safety limit value, wherein the second safety limit value is higher than the first safety limit value;
comparing the force or the variable with the second safety limit value; and
outputting a warning signal to an operator when the force or the variable is in a second prespecified relationship to the second safety limit value.

11. The method of claim 10, wherein the second prespecified relationship comprises the force or the variable being greater than the second safety limit value.

12. The method of claim 10, further comprising:
prespecifying a first value and a second value for the first safety limit value; and
selecting the first value or the second value as the first safety limit value based on the comparison with the force or the variable.

13. The method of claim 1, wherein the prespecifying of the first safety limit value depends on the acquired sensor values.

14. The method of claim 1, wherein the prespecifying of the first safety limit value is performed depending on:
a position, an orientation, or the position and the orientation of the function-specific end-effector of the kinematic chain,
a joint angle between two mobile components of the kinematic chain, or
the position, the orientation, or the position and the orientation of the function-specific end-effector of the kinematic chain and the joint angle between two mobile components of the kinematic chain.

15. The method of claim 14, further comprising:
checking to determine one predetermined spatial region of a plurality of predetermined spatial regions where the function-specific end-effector is located, wherein the prespecifying of the first safety limit value is performed depending on:
the position,
the orientation,
the position and the orientation,
the joint angle, or
the position, the orientation, and the joint angle.

16. The method of claim 1, wherein the adaptation includes: restricting a movement of the function-specific end-effector, a mobile component, or the function-specific end-effector and the mobile component by at least one joint; or
restricting a combined movement by a plurality of joints of the kinematic chain.

17. The method of claim 16, wherein the restricting comprises reducing the movement of the function-specific end-effector by a degree of freedom.

18. The method of claim 5, wherein the robotic device is a medical-robotic device used in a medical-surgical procedure, a medical-diagnostic procedure, or the medical-surgical procedure and the medical-diagnostic procedure.

19. The method of claim 18, wherein the robotic device comprises a holding device for an endoscope, a pedicle screw, a biopsy needle, or an ultrasound device.

20. The method of claim 18, wherein the prespecified force application, the prespecified torque application, or the prespecified force application and the prespecified torque application on the robotic device comprises:
a movement of a partial region of a patient, the partial region of the patient comprising a prespecified anatomical structure of the patient,
the robotic device acting on the partial region of a patient, or
the movement of the partial region of the patient and the robotic device acting on the partial region of the patient.

21. A robotic device comprising:
a kinematic chain of mobile components comprising a function-specific end-effector at one end;

a plurality of sensors arranged on the kinematic chain or in an environment of the kinematic chain, wherein the plurality of sensors is configured to acquire respective sensor values; and a control mechanism configured to:
  determine, based on the acquired sensor values, a force acting on the function-specific end-effector or another component of the kinematic chain, or a variable dependent on the force, in a prespecified manner;
  prespecify, automatically based on a medical-surgical or medical-diagnostic procedure, a first safety limit value based on a suitability of the function-specific end-effector of the kinematic chain for the procedure;
  compare the force or the variable with the prespecified first safety limit value; and
  adapt a characteristic of the kinematic chain or the function-specific end-effector when the force or the variable is in a prespecified relationship to the first safety limit value.

22. The method of claim 1, wherein the procedure specifies a region to be operated on by the function-specific end-effector.

23. The method of claim 21, wherein the procedure specifies a region to be operated on by the function-specific end-effector.

* * * * *